(12) United States Patent
Pazenok et al.

(10) Patent No.: US 8,258,335 B2
(45) Date of Patent: Sep. 4, 2012

(54) PROCESS FOR PREPARING 2-DIHALOACYL-3-AMINOACRYLIC ACID DERIVATIVES

(75) Inventors: Sergii Pazenok, Solingen (DE); Norbert Lui, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 129 days.

(21) Appl. No.: 12/679,709

(22) PCT Filed: Sep. 13, 2008

(86) PCT No.: PCT/EP2008/007612
§ 371 (c)(1),
(2), (4) Date: Mar. 24, 2010

(87) PCT Pub. No.: WO2009/043444
PCT Pub. Date: Apr. 9, 2009

(65) Prior Publication Data
US 2010/0204483 A1    Aug. 12, 2010

(30) Foreign Application Priority Data
Sep. 26, 2007    (EP) .................................... 07117232

(51) Int. Cl.
*C07C 229/00* (2006.01)
*C07C 255/01* (2006.01)
*C07C 231/00* (2006.01)
(52) U.S. Cl. ..................... 560/170; 558/303; 548/374.1
(58) Field of Classification Search ........................ None
See application file for complete search history.

(56) References Cited

U.S. PATENT DOCUMENTS

| 5,498,624 | A | 3/1996 | McLoughlin et al. |
| 6,706,911 | B1 | 3/2004 | Lui et al. |
| 7,358,387 | B2 * | 4/2008 | Lantzsch et al. ............ 560/170 |
| 7,884,216 | B2 * | 2/2011 | Umetani et al. ............ 548/373.1 |
| 2006/0116414 | A1 | 6/2006 | Dunkel et al. |
| 2006/0252944 | A1 | 11/2006 | Lantzsch et al. |
| 2010/0274049 | A1 * | 10/2010 | Lui et al. ...................... 562/553 |

FOREIGN PATENT DOCUMENTS

| EP | 1 000 926 | 5/2000 |
| WO | 03/051820 | 6/2003 |
| WO | 03/070705 | 8/2003 |
| WO | 2005/042468 | 5/2005 |
| WO | WO 2008102678 A1 * | 8/2008 |

OTHER PUBLICATIONS

International Search Report based on PCT/EP2008/007612 dated Nov. 21, 2008.
International Search Report based on PCT/EP2008/007612 dated Nov. 21, 2008 (3 pp.).
Beck et al.; "Synthesis of 1-(1,1-Dimethylethyl)-H-Pyrazole-4-Carboxylate Ester Derivatives"; J. Heterocyclic Chem., 24, 693 (1987).
England et al.; "Fluoroketenes. II.1 Difluoroketene"; The Journal of Organic Chemistry; vol. 33, No. 2; pp. 816-819; Feb. 1968.
England; "Catalytic Conversion of Fluoroalkyl Alkyl Ethers to Carbonyl Compounds"; The Journal of Organic Chemistry; vol. 49, pp. 4007-4008 (1984).
Bartnik et al.; "A New Synthesis of Enaminoketones"; Tetrahedron Letters; vol. 37; No. 48; pp. 8751-8754 (1996).
Rene et al.; "A One Pot Synthesis of Beta-Cyanoenamines"; Communications; pp. 419-420; May 1986.

* cited by examiner

*Primary Examiner* — Kamal Saeed
*Assistant Examiner* — Nyeemah A Grazier
(74) *Attorney, Agent, or Firm* — Baker Donelson Bearman; Caldewell & Berkowitz, PC

(57) ABSTRACT

The present invention relates to a process for preparing hydrochloride-free 2-dihaloacyl-3-aminoacrylic esters by reacting acid fluorides with dialkylaminoacrylic acid derivatives.

12 Claims, No Drawings

PROCESS FOR PREPARING 2-DIHALOACYL-3-AMINOACRYLIC ACID DERIVATIVES

CROSS REFERENCE TO RELATED APPLICATIONS

This application is a §371 National Stage Application of PCT/EP2008/007612 filed Sep. 13, 2008, which claims priority to European Application 07117232.4 filed Sep. 26, 2007.

BACKGROUND OF THE INVENTION

1. Field of the Invention

The present invention relates to a process for preparing hydrochloride-free 2-dihaloacyl-3-aminoacrylic esters by reacting acid fluorides with dialkylaminoacrylic acid derivatives.

2. Description of Related Art

2-Dihaloacyl-3-aminoacrylic esters of the formula (I) are valuable intermediates for the preparation of dihalomethyl-substituted pyrazolylcarboxylic acid derivatives, which can serve as precursors of active fungicidal ingredients (cf. WO 03/070705).

Tetrahedron Lett. 1996, 37, 8751-8754 already discloses that trihaloacylated aminoacrylic esters are obtained when the corresponding chloroacroleins are reacted with a substituted amine. The chloroacroleins required as starting materials are obtained from the corresponding trihaloacetoacetates by means of a Vilsmeier reaction. One disadvantage of this process is that phosphorus oxide trichloride has to be used in the Vilsmeier reaction, and another is that the overall yields are not satisfactory on the industrial scale.

EP-A-1 000 926 teaches that trihaloacylaminopropenoates are obtained by reacting trihaloacetoacetates with dialkylformamide acetals. A disadvantage here is that the deacylated compound occurs as a by-product and has to be removed from the desired product, which leads to additional costs and yield losses.

WO 03/051820 teaches that 2-perhaloacyl-3-aminoacrylic acid derivatives can be obtained by reacting 3-aminoacrylic esters with perhaloalkylcarboxylic anhydrides. However, the process described is not suitable for preparing dihaloacyl-substituted aminoacrylic acid derivatives, since hydrogen chloride is eliminated in the presence of an α-hydrogen, in the presence of tri-ethylamine The dihaloketenes thus formed are very unstable compounds (cf. J. Org. Chem. 1968, 33, 816), which tend to polymerize.

WO 2005/042468 discloses that 2-perhaloacyl-3-aminoacrylic acid derivatives can be obtained by reacting 3-aminoacrylic esters with acid halides in the presence of an organic base. These processes form equimolar amounts of salts, for example hydrochlorides, which have to be removed from the product by filtration or aqueous workup. If the term "hydrochlorides" is used hereinafter, in connection with the invention, the term shall encompass all impurities which form through the reaction with the base, for example hydrochlorides, HCl, other salts. Merely by filtration, however, the products cannot be removed fully from the hydrochlorides, and so certain amounts of the hydrochlorides remain in the product. In many cases, an aqueous workup is also unsuitable, since numerous 2-perhaloacyl-3-aminoacrylic acids, for example 2,2-difluoroacetyl-3-aminoacrylic acid, are hydrolysis-sensitive.

Moreover, the use of an organic base makes the process more expensive and leads to additional wastes.

The full removal of the hydrochlorides from the 2-perhaloacyl-3-aminoacrylic esters is, however, of great synthetic significance, since their reaction with alkylhydrazines impairs the regioselectivity of the ring closure as a result of the presence of HCl or hydrochlorides. For instance, it has been observed that, in the presence even of only small amounts of hydrochlorides, the proportion of the undesired regioisomeric 5-haloalkyl-4-carboxylic acid-pyrazole grows disproportionately.

For example, U.S. Pat. No. 5,498,624 teaches that 3-difluoromethylpyrazole derivatives can be obtained when 2-(difluoroacetyl)-3-alkoxyacrylates are reacted with hydrazines in protic solvents. Here too, the yields of the process leave something to be desired, since a high percentage of the undesired isomeric pyrazoles forms and the isolation of the desired isomers gives rise to further losses. The industrial employment of such a process is therefore scarcely possible for economic reasons.

The ring closure reaction of alkoxyacrylates with hydrazine derivatives forms a high percentage (up to 88%) of the undesired 5-haloalkyl-4-carboxylic acid-pyrazole (cf. J. Het. Chem. 1987, 24, 693).

The dihalomethylalkoxyacrylates are prepared from dihaloacetoacetic esters. Dihaloacetoacetic esters are commercially unavailable and their preparation is technically demanding, since it entails, for example, the use of ketene. The compounds are therefore not preparable in an economically viable manner.

WO 03/051820 discloses that 2-perhaloacyl-3-aminoacrylic acid derivatives can be reacted with hydrazines to give 3-perhalo-substituted pyrazoles. Although use of an aprotic solvent allows the formation of the undesired isomer to be lowered, it is still considerable on application to the inventive dihalogen compounds.

SUMMARY OF THE INVENTION

It was therefore an object of the present invention to provide novel and more economically viable processes by which 2-dihaloacyl-3-aminoacrylic esters which are free of the above-described hydrochloride impurities can be obtained with a high overall yield.

The object is achieved by a process for preparing 2-dihaloacyl-3-aminoacrylic acid derivatives of the formula (I)

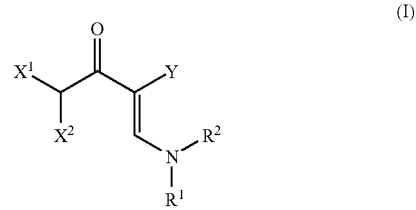

in which
R$^1$ and R$^2$ are each independently selected from C$_{1-12}$-alkyl radicals, C$_{5-18}$-aryl, C$_{7-19}$-alkylaryl and C$_{7-19}$-arylalkyl radicals; or
R$^1$ and R$^2$, together with the nitrogen atom to which they are bonded, may form a 5- to 6-membered ring which may optionally contain one or two further heteroatoms selected from O, S and an SO$_2$ group;
Y is selected from (C=O)OR$^3$, CN and (C=O)NR$^4$R$^5$, where R$^3$, R$^4$ and R$^5$ are each independently selected from C$_{1-12}$-alkyl radicals, C$_{5-18}$-aryl, C$_{7-19}$-alkylaryl and $C_{7-19}$-arylalkyl radicals, and $R^4$ and $R^5$, together with the nitrogen atom to which they are bonded and/or further atoms which are selected from C, N, O and S, may form a five- or six-membered ring which may be substituted by $C_{1-6}$-alkyl radicals;

$X^1$ and $X^2$ are each independently fluorine, chlorine, bromine and iodine, by reacting acid fluorides of the formula (II)

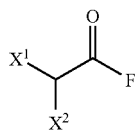

(II)

in which $X^1$ and $X^2$ are each as defined above with 3-aminoacrylic acid derivatives of the formula (III)

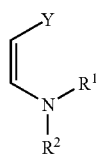

(III)

in which $R^1$, $R^2$ and Y are each as defined above, characterized in that the reaction is effected in the absence of bases.

DETAILED DESCRIPTION OF A PREFERRED EMBODIMENT

General Definitions

In connection with the present invention, the term halogens (X), unless defined otherwise, comprises those elements which are selected from the group consisting of fluorine, chlorine, bromine and iodine, preference being given to using fluorine, chlorine and bromine, and particular preference to using fluorine and chlorine.

Optionally substituted groups may be mono- or polysubstituted, and the substituents may be the same or different in the case of polysubstitutions.

Alkyl groups substituted by one or more halogen atoms (—X) are, for example, selected from trifluoromethyl ($CF_3$), difluoromethyl ($CHF_2$), $CF_3CH_2$, $ClCH_2$, $CF_3CCl_2$, $CF_3CHF$.

In connection with the present invention, unless defined otherwise, alkyl groups are linear, branched or cyclic saturated hydrocarbon groups.

The definition "$C_1$-$C_{12}$-alkyl" encompasses the largest range for an alkyl group defined herein. Specifically, this definition encompasses, for example, the meanings of methyl, ethyl, n- and isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined otherwise, alkenyl groups are linear, branched or cyclic hydrocarbon groups which contain at least one monounsaturation (double bond).

The definition "$C_2$-$C_{12}$-alkenyl" encompasses the largest range for an alkenyl group defined herein. Specifically, this definition encompasses, for example, the meanings of vinyl; allyl(2-propenyl), isopropenyl(1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In connection with the present invention, unless defined otherwise, alkynyl groups are linear, branched or cyclic hydrocarbon groups which contain at least one diunsaturation (triple bond).

The definition "$C_2$-$C_{12}$-alkynyl" encompasses the largest range for an alkynyl group defined herein. Specifically, this definition encompasses, for example, the meanings of ethynyl(acetylenyl); prop-1-ynyl and prop-2-ynyl.

In connection with the present invention, unless defined otherwise, aryl groups are aromatic hydrocarbon groups which may have one, two or more heteroatoms which are selected from O, N, P and S.

The definition "$C_{5-18}$-aryl" encompasses the largest range defined herein for an aryl group having 5 to 18 atoms. Specifically, this definition encompasses, for example, the meanings of cyclopentadienyl, phenyl, cycloheptatrienyl, cyclooctatetraenyl, naphthyl and anthracenyl.

In connection with the present invention, unless defined otherwise, arylalkyl groups (aralkyl groups) are alkyl groups substituted by aryl groups, which may have a $C_{1-8}$-alkylene chain and, in the aryl skeleton, may have one or more heteroatoms which are selected from O, N, P and S.

The definition "$C_{7-19}$-aralkyl group" encompasses the largest range defined herein for an arylalkyl group having a total of 7 to 19 atoms in the skeleton and alkylene chain. Specifically, this definition encompasses, for example, the meanings of benzyl- and phenylethyl.

In connection with the present invention, unless defined otherwise, alkylaryl groups (alkaryl groups) are aryl groups substituted by alkyl groups, which may have a $C_{1-8}$-alkylene chain and, in the aryl skeleton, may have one or more heteroatoms which are selected from O, N, P and S.

The definition "$C_{7-19}$-alkylaryl group" encompasses the largest range defined herein for an alkylaryl group having a total of 7 to 19 atoms in the skeleton and alkylene chain. Specifically, this definition encompasses, for example, the meanings of tolyl, 2,3-, 2,4-, 2,5-, 2,6-, 3,4- or 3,5-dimethylphenyl.

The inventive compounds may optionally be present in the form of mixtures of different possible isomeric forms, especially of stereoisomers, for example E and Z, threo and erythro, and also optical isomers, but if appropriate also of tautomers. Disclosed and claimed are both the E and the Z isomers, and also the threo and erythro isomers, and also the optical isomers, any desired mixtures of these isomers, and the possible tautomeric forms.

It has been found that 2-dihaloacyl-3-dialkylaminoacrylic acid derivatives prepared by the process according to the invention, which are free of hydrochloride impurities, can be converted with high yields and selectivities (ratio of 3-dihalomethyl-2H-pyrazole-4-carboxylic acid derivatives <<3-dihalomethyl-1H-pyrazole-4-carboxylic acid derivatives). The overall reaction follows the general reaction scheme 1.

Scheme 1

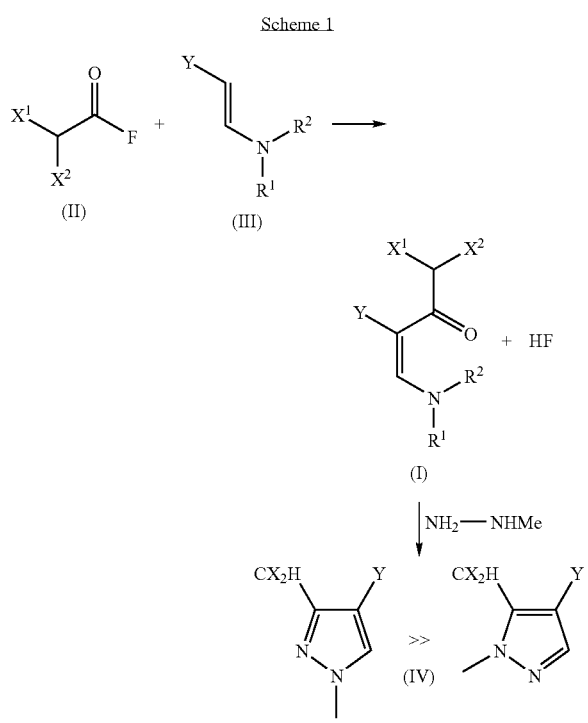

Acid Fluorides (II)

The acid fluorides used as starting materials in the performance of the process according to the invention are defined in general terms by the formula (II). In formula (II), the $X^1$ and $X^2$ radicals are each independently fluorine, chlorine, bromine and iodine, is preferably fluorine, chlorine and bromine; more preferably, both groups are fluorine.

Acid fluorides of the formula (II) are known synthesis chemicals and can be prepared, for example, in a simple manner from tetrafluoroethyl methyl ethers, according to scheme III (D. England, J. Org. Chem. 1984, 49, 4007-4008).

Scheme III

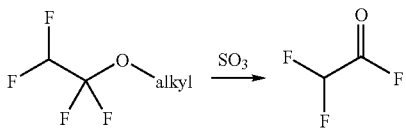

Dialkylaminoacrylic Acid Derivatives (III)

The dialkylaminoacrylic acid derivatives used as starting materials in the performance of the process according to the invention are defined in general terms by the formula (III). In this formula, $R^1$ and $R^2$ may each independently be selected from $C_{1-12}$-alkyl radicals, $C_{5-18}$-aryl, $C_{7-19}$-alkylaryl and $C_{7-19}$-arylalkyl radicals, or $R^1$ and $R^2$, together with the nitrogen atom to which they are bonded, may form a 5- to 6-membered ring which may optionally contain one or two further heteroatoms selected from O, S and an $SO_2$ group, Y may be selected from carboxylic ester groups ((C=O)$OR^3$), nitrile groups (CN) and amide groups ((C=O)$NR^4R^5$), where $R^3$, $R^4$ and $R^5$ are each independently selected from $C_{1-12}$-alkyl radicals, $C_{5-18}$-aryl, $C_{7-19}$-alkylaryl and $C_{7-19}$-arylalkyl radicals, and $R^4$ and $R^5$, together with the nitrogen atom to which they are bonded and/or further atoms which are selected from C, N, O and S, may form a five- or six-membered ring which may be substituted by $C_{1-6}$-alkyl radicals.

Preferably,
$R^1$ and $R^2$ may each independently be selected from methyl, ethyl, n-propyl and isopropyl,
$R^1$ and $R^2$, together with the nitrogen atom to which they are bonded, may form a piperidinyl or pyrrolidinyl ring,
Y may be selected from (C=O)$OR^3$ where $R^3$ is selected from methyl, ethyl, n-propyl and isopropyl.
More preferably,
$R^1$ and $R^2$ may each be methyl and
Y may be —(C=O)$OC_2H_5$.

Dialkylaminoacrylic esters of the formula (III) are known synthesis chemicals and are commercially available.

Examples of dialkylaminoacrylic esters suitable in accordance with the invention are methyl 3-(N,N-dimethylamino)acrylate, ethyl 3-(N,N-dimethylamino)acrylate, ethyl 3-(N,N-diethylamino)acrylate, 3-(N,N-dimethylamino)acrylonitrile, N,N-dimethyl-3-(N,N-dimethylamino)acrylamide and N,N-diethyl-3-(N,N-dimethylamino)acrylamide, particular preference being given to ethyl 3-(N,N-dimethylamino)acrylate.

Processes for preparing dialkylaminoacrylic esters have been described before in the prior art, for example in EP-A-0 608 725.

Processes for preparing dialkylaminoacrylonitriles are described in the prior art, for example by Rene et al. in Synthesis (1986), (5), 419-420.

The dialkylaminoacrylic acid derivatives may, if necessary, for example, be purified by distillation. However, this is generally not required in connection with the inventive reaction.

The molar ratio of dialkylaminoacrylic acid derivatives (III) to acid fluorides (II) used may, for example, be 0.5 to 3, preferably 0.8 to 2, more preferably 1.0 to 1.5.

The process according to the invention is preferably carried out in an organic diluent/solvent. Particularly suitable examples for this purpose are aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane. Particular preference is given to using toluene, xylene, chlorobenzene, n-hexane, cyclohexane or methylcyclohexane, very particular preference to using toluene, chlorobenzene, acetonitrile or xylene, nitriles, amides, ethers.

The process according to the invention is performed in the absence of bases, i.e. without addition of one or more bases. In connection with the process according to the invention, "base" may be any inorganic or organic base.

Examples of organic bases are tertiary nitrogen bases, for example tertiary amines, substituted or unsubstituted pyridines and substituted or unsubstituted quinolines, triethylamine, trimethylamine, diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3-, 4-picoline, 2-methyl-5-ethylpyridine, 2,6-lutidine, 2,4,6-collidine, 4-dimethylaminopyridine, quinoline, quinaldine, N,N,N,N-tetramethylethyldiamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN) and diazabicycloundecane (DBU).

Examples of inorganic bases are alkali metal or alkaline earth metal hydroxides, hydrogencarbonates or carbonates and other inorganic aqueous bases; preference is given, for example, to sodium hydroxide, potassium hydroxide, lithium hydroxide, calcium hydroxide, sodium carbonate, potassium carbonate, sodium hydrogencarbonate, potassium hydrogencarbonate and sodium acetate.

In order to prevent the formation of salts, for example of hydrochlorides, the process is performed in the absence of bases. This means that, more preferably, no bases are present in the reaction mixture. In practice, traces of bases which are present as impurities will be unavoidable. "Base-free" therefore means that the proportion of bases in the reaction mixture is not greater than 1%, preferably not greater than 0.1%, more preferably not greater than 0.01%, based on the reaction mixture.

When the process according to the invention is performed, it is necessary to work within a relatively small temperature range. The working temperatures are generally −50 to 100° C., preferably −20° C. to +50° C., more preferably temperatures of −10° C. to +45° C.

The process according to the invention is generally carried out under standard pressure. However, it is also possible to work under elevated pressure, for example when the volatile difluoroacetyl fluoride is used. In this connection, elevated pressure means 0.1 to 5 bar, preferably 0.15 to 4 bar, more preferably 0.2 to 1 bar.

The reaction time is not critical and can be selected within a relatively wide range according to the batch size. In principle, the reaction time is in the range from 30 minutes up to 4 h, preferably between 45 min and 2 h.

In the performance of the process according to the invention (a), for 1 mol of acid fluoride of the formula (II), generally between 0.5 mol and 3 mol, preferably between 0.5 mol and 1.5 mol and more preferably between 0.9 mol and 1.0 mol of a dialkylaminoacrylic acid derivative of the formula (III) are used.

After the reaction has ended, the reaction mixture can in principle be used in the next reaction stage (pyrazole synthesis) without further purification. It is considered to be surprising that HF or HF salts do not impair the regioselectivity of the cyclization with alkylhydrazines, especially as compared with HCl or the corresponding hydrochlorides. Consequently, the process can be performed without intermediate isolation of the 3-dihalomethyl-1H-pyrazole-4-carboxylic acid derivatives of the formula (I) as a one-pot reaction.

Even when the reaction is carried out in the presence of a base, the removal of HF salts is likewise unnecessary. Consequently, the reaction with the alkylhydrazines, preferably with methylhydrazine, can likewise be performed without yield losses.

PREPARATION EXAMPLES

Example 1

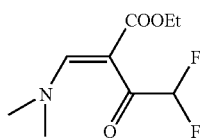

71.6 g (0.5 mol) of ethyl dimethylaminoacrylate are dissolved in 150 ml of toluene and the mixture is cooled to 0° C. Subsequently, within 30-40 min at 0-3° C., 50 g (0.5 mol) of difluoroacetyl fluoride are introduced into the solution with stirring. After stirring at 0-3° C. for 3 h, the mixture is warmed to room temperature. After complete removal of the solvent under reduced pressure (10 mbar), 105 g (95% of theory) of ethyl 2-(difluoroacetyl)-3-(dimethylamino)acrylate are obtained in a purity of 98 area % (GC analysis).

$^1$H NMR (CD$_3$CN): δ=7.88 (s, 1H), 6.47, 6.61 and 6.74 (t, 1H), 4.13-4.19 (m, 2H), 3.32 (s, 3H), 2.85 (s, 3H), 1.25-1.28 (t, 3H) ppm.

Example 2

71.6 g (0.5 mol) of ethyl dimethylaminoacrylate are dissolved in 150 ml of toluene and admixed with 0.5 mol of triethylamine, and the mixture is cooled to 0° C. Subsequently, within 30-40 min at 0-3° C., 50 g (0.5 mol) of difluoroacetyl fluoride are introduced into the solution with stirring. After stirring at 0-3° C. for 3 h, the reaction mixture is warmed to room temperature. After complete removal of the solvent under reduced pressure (10 mbar), 108 g (98% of theory) of ethyl 2-(difluoroacetyl)-3-(dimethylamino)acrylate are obtained in a purity of 98 area % (GC analysis).

$^1$H NMR (CD$_3$CN): δ=7.88 (s, 1H), 6.47, 6.61 and 6.74 (t, 1H), 4.13-4.19 (m, 2H), 3.32 (s, 3H), 2.85 (s, 3H), 1.25-1.28 (t, 3H) ppm.

Example 3

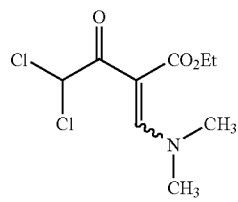

71.6 g (0.5 mol) of ethyl dimethylaminoacrylate are dissolved in 150 ml of toluene and added dropwise with stirring at 0-3° C. to a solution of 73.7 g (0.5 mol) of dichloroacetyl fluoride. After stirring at 0-3° C. for 3 h, the reaction mixture is warmed to room temperature. After complete removal of the solvent under reduced pressure (10 mbar), 114 g (90% of theory) of ethyl 2-(dichloroacetyl)-3-(dimethylamino)acrylate are obtained (m.p. 71-72° C.).

Example 4

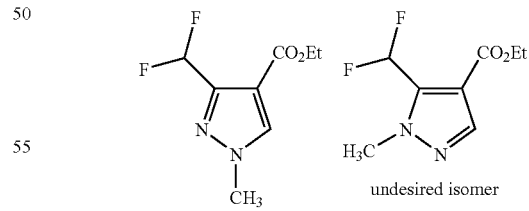

undesired isomer 71.6 g (0.5 mol) of ethyl dimethylaminoacrylate are dissolved in 150 ml of toluene. After cooling the mixture to 0° C., 50 g (0.5 mol) of difluoroacetyl fluoride are introduced into the solution with stirring at 0-3° C. within 30-40 min. Thereafter, the mixture is stirred at 0-3° C. for 3 h, then cooled to −20° C. At this temperature, 26.4 g of methylhydrazine are slowly added dropwise. Subsequently, the mixture is stirred at 0° C. for a further 3 h, warmed to room temperature and finally stirred at 20-25° C. for 1 h.

After adding 500 ml of water, the toluene phase is removed and the water phase is extracted twice more with 100 ml of toluene each time. After the combined toluene phases have been concentrated, ethyl 3-(difluoromethyl)-1-methyl-1H-pyrazole-4-carboxylate (yield: 89% of theory) is obtained in a mixture with the undesired isomer [ethyl 5-(difluoromethyl)-1-methyl-1H-pyrazole-4-carboxylate] in a ratio of 91:9 (GC-MS analysis). Washing with hexane allows the undesired isomer to be removed fully. Yield: 85%.

The invention claimed is:

1. Process for preparing a 2-dihaloacyl-3-aminoacrylic ester of formula (I)

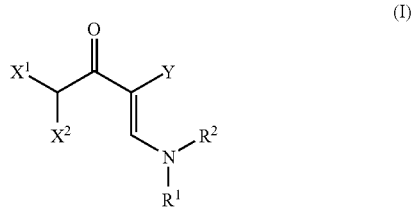

(I)

in which
- $R^1$ and $R^2$ are each independently selected from $C_{1-12}$-alkyl radicals, $C_{5-18}$-aryl, $C_{7-19}$-alkylaryl and $C_{7-9}$-arylalkyl radicals, or
- $R^1$ and $R^2$, together with the nitrogen atom to which they are bonded, may form a 5- to 6-membered ring which may optionally contain one or two further heteroatoms selected from O, S and an $SO_2$ group,
- Y is selected from $(C=O)OR^3$, CN and $(C=O)NR^4R^5$, where $R^3$, $R^4$ and $R^5$ are each independently selected from $C_{1-12}$-alkyl radicals, $C_{5-18}$-aryl, $C_{7-19}$-alkylaryl and $C_{7-19}$-arylalkyl radicals, and $R^4$ and $R^5$, together with the nitrogen atom to which they are bonded and/or further atoms which are selected from C, N, O and S, may form a five- or six-membered ring which may be substituted by $C_{1-6}$-alkyl radicals; and
- $X^1$ and $X^2$ are each independently fluorine, chlorine, bromine and iodine, said process comprising reacting an acid fluoride of formula (II)

(II)

with a 3-aminoacrylic acid derivative of formula (III)

(III)

wherein the reaction is effected in the absence of a base.

2. Process according to claim 1, wherein
- $R^1$ and $R^2$ are each independently selected from methyl, ethyl, n-propyl and isopropyl, or
- $R^1$ and $R^2$, together with the nitrogen atom to which they are bonded, form a piperidinyl or pyrrolidinyl ring,
- Y is selected from $(C=O)OR^3$ where $R^3$ is selected from methyl, ethyl, n-propyl and isopropyl,
- $X^1$ and $X^2$ are each independently selected from fluorine, chlorine and bromine.

3. Process according to claim 1, wherein
- $R^1$ and $R^2$ are each methyl,
- Y is $(C=O)OC_2H_5$ and
- $X^1$ and $X^2$ are both fluorine.

4. Process according to claim 1, wherein the 3-aminoacrylic acid derivative is selected from the group consisting of methyl 3-(N,N-dimethylamino)-acrylate, ethyl 3-(N,N-dimethylamino)acrylate, ethyl 3-(N,N-diethylamino)acrylate, 3-(N,N-dimethylamino)acrylonitrile, N,N-dimethyl-3-(N,N-dimethylamino)acrylamide and N,N-diethyl-3-(N,N-dimethylamino)acrylamide.

5. Process according to claim 1, wherein the reaction is effected in an organic solvent.

6. Process according to claim 2, wherein
- $R^1$ and $R^2$ are each methyl,
- Y is $(C=O)OC_2H_5$ and
- $X^1$ and $X^2$ are both fluorine.

7. Process according to claim 2, wherein the 3 aminoacrylic acid derivative is selected from the group consisting of methyl 3-(N,N-dimethylamino)-acrylate, ethyl 3-(N,N-dimethylamino)acrylate, ethyl 3-(N,N-diethylamino)acrylate, 3-(N,N-dimethylamino)acrylonitrile, N,N-dimethyl-3-(N,N-dimethylamino)acrylamide and N,N-diethyl-3-(N,N-dimethylamino)acrylamide.

8. Process according to claim 3, wherein the 3 aminoacrylic acid derivative is selected from the group consisting of methyl 3-(N,N-dimethylamino)-acrylate, ethyl 3-(N,N-dimethylamino)acrylate, ethyl 3-(N,N-diethylamino)acrylate, 3-(N,N-dimethylamino)acrylonitrile, N,N-dimethyl-3-(N,N-dimethylamino)acrylamide and N,N-diethyl-3-(N,N-dimethylamino)acrylamide.

9. Process according to claim 2 wherein the reaction is effected in an organic solvent.

10. Process according to claim 3 wherein the reaction is effected in an organic solvent.

11. Process according to claim 4 wherein the reaction is effected in an organic solvent.

12. Process according to claim 1, wherein the 3-aminoacrylic acid derivative is ethyl 3-(N,N-dimethylamino)-acrylate.

* * * * *